United States Patent [19]

Van Der Jagt

[11] Patent Number: Plant 6,483

[45] Date of Patent: Dec. 20, 1988

[54] CHRYSANTHEMUM NAMED "RECORD"

[75] Inventor: Martinus Van Der Jagt, Ter Aar, Netherlands

[73] Assignee: Chrysanthemum Breeders Association, N.V., Curacao, Netherlands Antilles

[21] Appl. No.: 3,544

[22] Filed: Jan. 15, 1987

[51] Int. Cl.[4] ..... A01H 5/00

[52] U.S. Cl. ..... Plt./80

[58] Field of Search ..... Plt./76, 80

*Primary Examiner*—Robert E. Bagwill

*Attorney, Agent, or Firm*—Parkhurst & Oliff

[57] ABSTRACT

A new and distinct cultivar of Chrysanthemum plant named Record, bearing medium sized red blossoms with a greyed red center and a performance of twenty days.

3 Drawing Sheets

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a cross of unknown parents (mixed pollination, mixed harvesting). The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and greyed red color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage of the new cultivar.

DESCRIPTION OF THE NEW PLANT

This new variety of Chrysanthemum is of the botanical classification *Chrysanthemum morifolium,* named Record. When grown in the vicinity of Ter Aar, Holland, It has a response time of approximately eight weeks. This new variety produces medium sized red blooms with a greyed red center having a performance of twenty days. This new variety of Chrysanthemum has been found to retain its distinctive characteristics throughout successive propagations and may be planted under conventional greenhouse conditions in Holland between weeks 1 and 40.

The following is a description of the plant and characteristics that distinguish it over related known varieties and its antecedents:

Botanical classification: *Chyrsanthemum morifolium.*

Bud:
- *Size.*—Large (cross section: 1.5 cm, height: 1.3 cm).
- *Form.*—Round and flat.
- *Outside color.*—Greyed red 168A.

Bloom:
- *Size.*—Medium.
- *Fully expanded.*—8–8.5 cm.
- *Borne.*—Single.
- *Stem.*—Strong.
- *Forms.*—Decorative.
- *Permanence.*—Excellent, 20 days.

Color:
- *Center of flower (disk floret).*—Greyed red 168A.
- *Base of petals.*—Greyed red 180D.
- *Inside of petals.*—Greyed purple 181D.
- *Reverse of petals.*—Greyed red 181D.
- *Outer petals.*—Greyed red 181D.
- *Tonality from a distance.*—A greyed red/purple "spider-like" decorative flower being a rather unique flower form.
- *Discoloration.*—To a greyed red 181D upon maturity.

Petals:
- *Texture.*—Upper side: Rough. Underside: Rough.
- *Number.*—(Excluding the unfurled center) approx. 80–100.
- *Cross-section.*—Tubular, flat at the end (spoon form).
- *Arrangement.*—Imbricated.
- *Persistence.*—Excellent.
- *Fragrance.*—Chrysanthemum.

Reproductive organs:
- *Stamens.*—Sometimes in the petals.
- *Pollen.*—None.
- *Styles.*—Sometimes in the petals, very thin and short (2 mm).
- *Stigmas.*—Green, width: 0.7 mm.
- *Ovaries.*—Enclosed in calyx.

Plant:
- *Form.*—Spray mum meant for erect culture.
- *Growth.*—Good.
- *Height.*—100 cm.
- *Peduncle.*—Near the top: 9 cm. Near the middle: 20 cm. Near the bottom: 23 cm.
- *Internodes.*—2.5–3 cm.
- *Flowering response.*—8 weeks.

Foliage:

*Color.*—Upperside: Green 147A. Underside: Green 147B.

*Size.*—Length: 11 cm, width: 8 cm.

*Quantity.*—35–40.

*Shape.*—Oval, not undulated.

*Texture.*—Upperside: Very rough. Underside: Rough; minimally hirsute.

*Ribs and veins.*—Average number of ribs, a high number of veins. Upperside: Ribs not so clear to see, veins clear to see. Underside: Both ribs and veins clear to see.

*Edge.*—Straight.

In the description above, color references are made to the "R.H.S. Colour Chart" issued by The Royal Horticultural Society, in association with the Flower Council of Holland, Edition February 1986.

What is claimed:

1. A new and distinct cultivar of Chrysanthemum named Record, as described and illustrated in the foregoing specification and accompanying drawings.

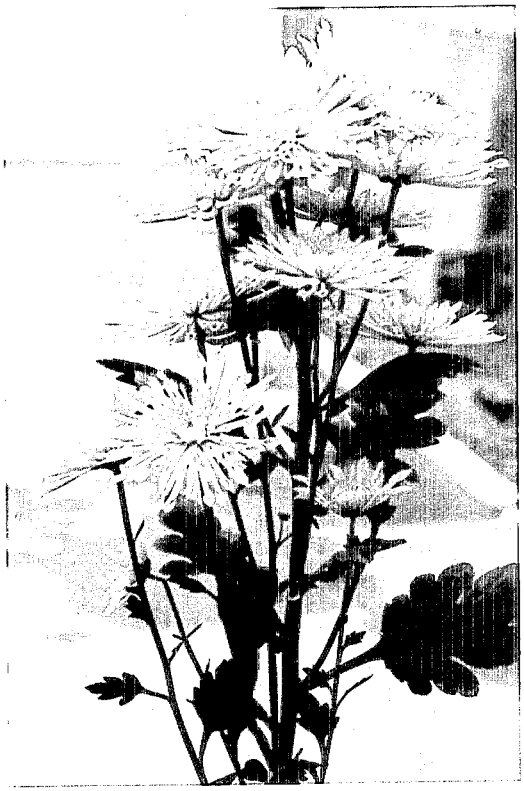

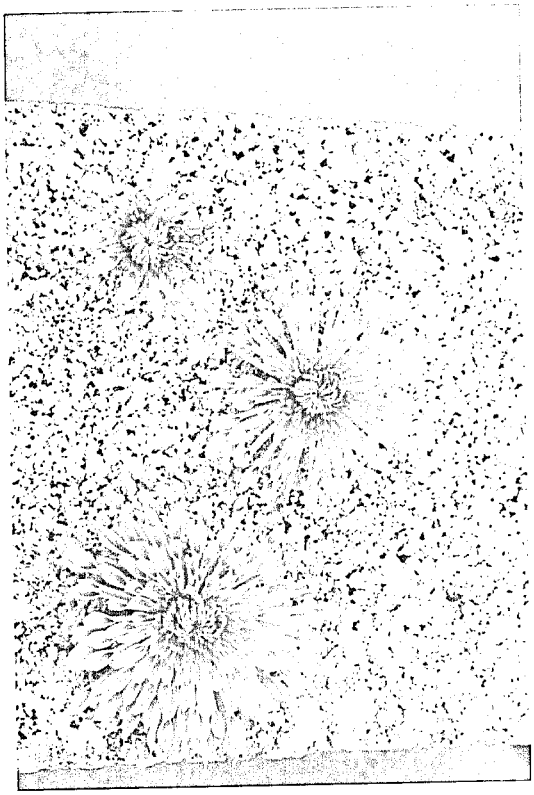

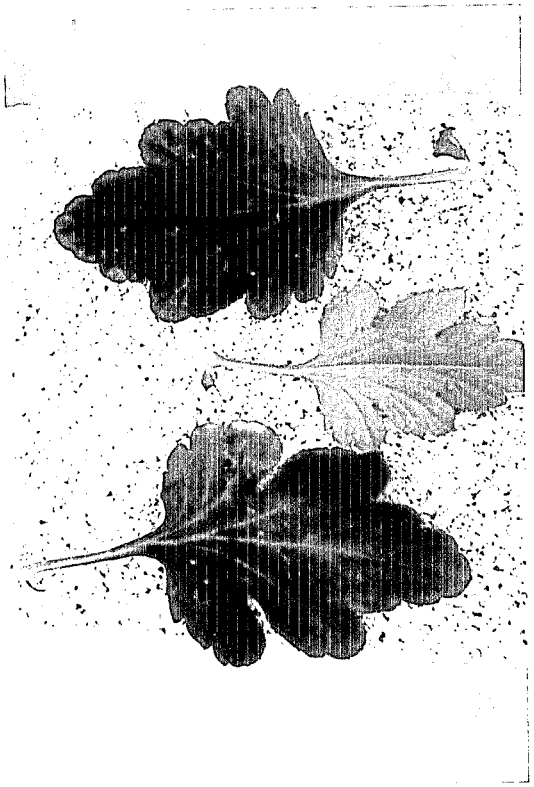

* * * * *